United States Patent [19]

Chandross et al.

[11] Patent Number: 4,666,820

[45] Date of Patent: May 19, 1987

[54] PHOTOSENSITIVE ELEMENT COMPRISING A SUBSTRATE AND AN ALKALINE SOLUBLE MIXTURE

[75] Inventors: Edwin A. Chandross, Berkeley Heights; Elsa Reichmanis, Piscataway; Cletus W. Wilkins, Jr., Westfield, all of N.J.

[73] Assignee: American Telephone and Telegraph Company, AT&T Laboratories, Murray Hill, N.J.

[21] Appl. No.: 764,612

[22] Filed: Aug. 12, 1985

Related U.S. Application Data

[60] Division of Ser. No. 489,796, Apr. 29, 1983, Pat. No. 4,551,416, which is a continuation-in-part of Ser. No. 265,554, May 22, 1981, Pat. No. 4,400,461.

[51] Int. Cl.$^4$ ............................................. G03C 1/76
[52] U.S. Cl. ...................... 430/270; 430/272; 430/311; 430/320; 430/326; 522/65; 522/126
[58] Field of Search .................... 204/159, 159.22; 430/270, 272, 311, 320, 326, 325; 522/65, 126

[56] References Cited

U.S. PATENT DOCUMENTS

| | | | |
|---|---|---|---|
| 3,849,137 | 11/1974 | Barzynski et al. | 430/281 |
| 3,949,143 | 4/1976 | Schlesinger | 430/270 |
| 4,131,465 | 12/1978 | Petropoulos | 430/270 |
| 4,150,989 | 4/1979 | Chambers et al. | 430/270 |
| 4,440,461 | 8/1983 | Chandross et al. | 430/311 |
| 4,551,416 | 11/1985 | Chandross et al. | 430/271 |

*Primary Examiner*—Jack P. Brammer
*Attorney, Agent, or Firm*—Bernard Tiegerman

[57] ABSTRACT

Photosensitive bodies that are sensitive to ultraviolet radiation and that exhibit excellent contrast are formed from base soluble polymers such as poly(methyl methacrylate-co-methacrylic acid) physically mixed with base insoluble materials such as o,o'-dinitrobenzyl esters. The base insoluble esters decompose upon irradiation to form base soluble entities in the irradiated regions. These irradiated portions are then soluble in basic solutions that are used to develop the desired image.

7 Claims, No Drawings

PHOTOSENSITIVE ELEMENT COMPRISING A SUBSTRATE AND AN ALKALINE SOLUBLE MIXTURE

This application is a division of Ser. No. 489,796 filed Apr. 29, 1983 and now U.S. Pat. No. 4,551,416 which is a continuation-in-part Ser. No. 265,554 filed May 22, 1981 now U.S. Pat. No. 4,400,461.

BACKGROUND OF THE INVENTION

1. Field of the Invention

This invention relates to photosensitive bodies and, in particular, photosensitive bodies that yield positive images.

2. Art Background

Photosensitive bodies are utilized in many lithographic processes such as those involved in semiconductor device fabrication. Generally, the photosensitive body is produced by depositing an appropriately chosen photosensitive material on a substrate, e.g., a silicon wafer. One widely used material involves a physical mixture of a novolak resin such as one formed from cresols and formaldehyde with an insoluble photosensitive inhibitor such as a substituted o-naphthoquinone diazide. The novolak resin is chosen to be soluble in an alkaline solution. The inhibitor is chosen to be insoluble in an alkaline solution in its initial form, but soluble after it has undergone a chemical reaction induced by actinic radiation. In the case of a novolak resin and an o-naphthoquinone diazide inhibitor, upon irradiation with visible light, the inhibitor eliminates nitrogen and forms an indene carboxylic acid. Both the indene carboxylic acid and the resin are base soluble and, therefore, the total mixture is soluble in the areas that are irradiated. The final image is formed by treating these irradiated areas with an alkaline developer.

The previously described photosensitive materials, although quite useful, have some shortcomings. The potential for higher resolution is afforded by the use of short wavelength radiation such as ultraviolet radiation of wavelength less than 300 nm. However, novolak resins are highly absorbing in this portion of the ultraviolet region of the light spectrum. Sufficient incident ultraviolet light for exposure is thus essentially prevented from reaching the lower portion of the material thickness. For this reason, exposure through the thickness of the material for conventional photosensitive bodies having thicknesses greater than 0.5 $\mu$m is not practical with ultraviolet radiation of wavelengths less than 300 nm.

Additionally, the contrast of inhibited novolak resins is generally less than 2.5. (For a definition of contrast see *UV Curing:Science and Technology*, S. P. Pappas, Ed., page 333, Technology Marketing Corp., (1978).) Although this is useful for many applications better contrast is often desirable because it leads to higher image quality. This is especially significant at higher resolution facilitated by the use of short wavelength ultraviolet exposing radiation.

A photosensitive material has been made by converting a base soluble polymer, such as poly(methyl methacrylate-co-methacrylic acid) P(MMA-MAA), that has negligible absorption for radiation of wavelength longer than 230 nm, to a base insoluble polymer by esterification of the carboxylic acid groups with o-nitrobenzyl alcohol to produce a polymer represented by the formula

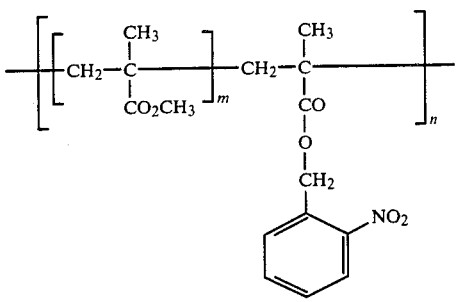

Although no experimental details have been reported, this material is expected to allow absorption of ultraviolet radiation (250 to 300 nm) completely through typical thicknesses. The contrast has not been disclosed. The contrast of any particular organic resist is not predictable and contrast values above 2.5 for organic resists are essentially unknown. There is an absence of photosensitive materials reported to have a high contrast known to be adaptable to ultraviolet (wavelength less than 300 nm) exposure through typical film thicknesses and thus capable of allowing the potential for higher resolution such exposure offers.

SUMMARY OF THE INVENTION

A high contrast (as high as 6) photosensitive composition that has a suitable absorption coefficient in the ultraviolet region of the spectrum in the range 220 to 300 nm is formed by physically mixing a base soluble polymer such as P(MMA-MAA) with an inhibitor including an o-nitroarylmethyl ester of a carboxylic acid, e.g., o-nitrobenzyl cholate. The subject physical mixtures have shown surprisingly high contrasts, e.g., as high as 6.

In use, the physical mixture is coated on a substrate by techniques such as spinning a solution of the mixture in an appropriate solvent to form a photosensitive body. The photosensitive body is then exposed, generally with UV light, to produce a desired image. (The absorption in a given wavelength range is adjustable by varying the structure of the inhibitor and, in fact, inhibitors absorbing in a portion of the visible as well as the ultraviolet range of 220 to 300 nm are also possible.) The photosensitive body is then developed by treatment with an alkaline solution such as an aqueous alkaline solution, e.g., an aqueous $Na_2CO_3$ or $NaHCO_3$ solution.

DETAILED DESCRIPTION

As previously discussed, the photosensitive composition used in the subject invention is base insoluble before irradiation with actinic radiation and soluble in base after exposure. If the ratio of the rate of solution of the photosensitive composition before irradiation compared to that after irradiation is taken as 1:n, n should not be less than 4 and preferably more than 10. Relative solubility rate ratios with values of n less than 4 produce low contrast and inferior image quality. This leads to substantially degraded resolution since upon development the exposed and unexposed regions dissolve at too similar a rate.

The solution rate of the photosensitive material both before and after exposure depends on (1) the rate of solution of the inhibitor which changes upon exposure and (2) the rate of solution of the polymer which is generally unchanged by exposure. Generally, it is desirable to use the smallest possible mole fraction of inhibitor in the photosensitive material to yield the desired result. The larger the mole fraction of inhibitor the higher the dose of radiation required to convert the inhibitor so that adequate solubility in the irradiated areas is achieved. Thus, sensitivity decreases as inhibitor mole fraction increases and to obtain the highest sensitivity it is desirable to use the least amount of inhibitor that leads to the desired contrast. Because of the wide range of base soluble polymers and suitable o-nitroarylmethyl ester inhibitors that are possible, the exact ratio of polymer to inhibitor material in the final photosensitive material should be determined by using a control sample. However, for typical inhibitors, such as o-nitrobenzyl cholate derivatives, and polymers, such as P(MMA-MAA), the amount of inhibitor added to a given amount of polymer should be in the range 5 to 40 weight percent, preferably 10 to 30 weight percent.

The inhibitor should be chosen so that it is represented by the formula

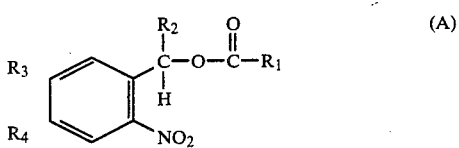

(A)

Upon irradiation the inhibitor fragments to form

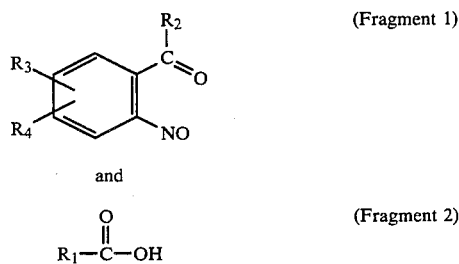

(Fragment 1)

and (Fragment 2)

$$R_1-\overset{O}{\underset{\|}{C}}-OH$$

Both fragments should be chosen so as to have sufficient solubility so that the previously defined relative solubility rates are achievable to yield the desired contrast. Additionally, the solubility after exposure should be sufficient to allow solution of the exposed region of the photosensitive material through its thickness. Except for very insoluble photosensitive materials, satisfying the former criterion also satisfies the latter. Fragment 2 is a carboxylic acid and, thus, with rare exception is base soluble. However, its degree of solubility in a given developer varies with $R_1$. Additionally, as discussed below, if Fragment 1 is a particularly large insoluble entity, no substantial increase in the rate of solubility of the irradiated composition will occur. That is, if Fragment 1 is sufficient insoluble, the effect of the solubility of Fragment 2 is overcome and undesirable results are produced.

To identify $R_1$ substituents which yield an inhibitor that satisfies the comparative rate of solubility requirements as previously defined ($n \geq 4$), $R_1$ should generally be chosen so that the corresponding salt, i.e.,

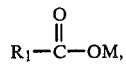

where M is, for example, a cation such as Li, Na, K, ammonium, or a substituted ammonium ion, has an aqueous solubility sufficient to permit formation of an aqueous solution having a concentration of at least 0.01M. If this measure of solubility is not satisfied, then there generally will be insufficient change in the solubility of the exposed region to yield the desired ratio of solubility rates. Typically, the greater the volume fraction of the photosensitive material that is altered from a base resistant state to a base soluble state by irradiation, the greater will be the difference in solubility after exposure. To satisfy the solubility difference criterion, it is advantageous to employ relatively large $R_1$ substituents. For example, $R_1$COOH (Fragment 2) species such as cholic acid, deoxycholic acid, lithocholic acid, and 5β-cholanic acid are utilized. It is advantageous to employ $R_1$ substituents that are predominantly hydrophobic in nature but have some polar groups. (Generally, a molecule that is predominantly a hydrocarbon is employed to yield the desired hydrophobic character. The more hydrophobic the $R_1$ group, the less permeable the resist is to the developer.) The polar groups are preferably positioned in the $R_1$ group to be remote from the carboxylic acid function. The polar substituents on the predominantly hydrophobic substituent enhance the solubility of the carboxylic acid fragment produced by radiation. However, the polar group employed should not be so hydrophilic that the developer tends to penetrate the unirradiated region. For example, cholic acid is more soluble in aqueous base than cholanic acid and the use of the o-nitrobenzyl ester of cholic acid yields higher sensitivity and contrast in several polymer matrices. If, however, more than a minimal mole fraction of carboxylic acid groups are present in the polymer, it is desirable to esterify some or all of the hydroxyl groups of the cholic acid so that good solubility in basic solution is maintained, but hydrophilicity is sufficiently reduced so that the unirradiated regions are more resistant to the developer. In this manner, contrast is enhanced while sensitivity is maintained.

A variety of o-nitroarylmethyl esters as shown in formula A, derived from alcohols as those described in U.S. Pat. No. 3,849,137, issued Nov. 19, 1974, which is hereby incorporated by reference, and those alcohols described by V. N. Rajasekharan Phillai in *Synthesis*, 1, (1980), are employable, provided the desired relative solubilities are obtained. It is possible that $R_3$ and $R_4$ are joined to form an aromatic ring system including the phenyl ring of the ortho-nitro ester. Typically, however, o-nitrobenzyl substituted aromatic compounds that have more than three fused rings produce a composition after exposure that has insufficient solubility in basic solution. Similarly, compounds having $R_3$ and $R_4$ as hydrogens or as other substituents on the aromatic ring of the inhibitor are not precluded. (The choice of $R_3$ and $R_4$ is typically not critical. For example, use of a wide range of groups such as H, lower alkoxy carbonyl, halogens, and lower alkyls are acceptable.) For the same reason $R_2$ is preferably H, or lower alkyls such as methyl and ethyl. However, substituents that substantially decrease the solubility of the exposed inhibitor should not be employed. Again, the basic requirement is that neither fragment produced should be so slow to dissolve in basic solution that the desired relative rates of solubility as previously discussed are not achievable.

It has been found that particularly advantageous sensitivity is achieved by employing an o,o'-dinitroarylmethyl ester, a species of the generic material represented by Formula A, which species is represented by the formula

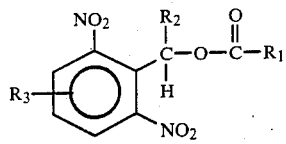

While the above formula shows only four substituents attached to the benzene ring, further substitution is not precluded. The $R_1$, $R_2$, and $R_3$ substituents (as well as any additional substituents) are chosen so as to satisfy the above-described solubility rate requirement and are advantageously the specific substituents previously described for $R_1$, $R_2$, $R_3$, and $R_4$. An exemplary ester having ortho-nitro groups is o,o'-dinitrobenzyl cholate, whose sensitivity is more than 40 percent higher than that of o-nitrobenzyl cholate.

The range of useful wavelengths employed in exposing the subject photosensitive material is modifiable by including in the inhibitor an acid component that absorbs in a desired wavelength range longer than that of the o-nitroarylmethyl moiety absorption. For example, absorption out to 400 nm is possible by using an acid component such as 9-fluorenone-4-carboxylic acid,

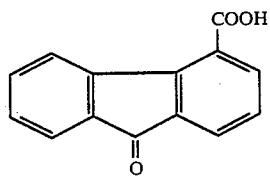

to form an inhibitor such as the o-nitrobenzyl ester of this acid. The chromophore in the acid group serves as a photosensitizer and, thus, the sensitivity range of a photosensitive moiety such as an o-nitrobenzyl group which typically absorbs only weakly at wavelengths longer than 300 nm is significantly extended. Generally, however, absorption of light of wavelength longer than 450 nm is not practical for image formation. Similarly, use of $R_1$ or $R_2$ substituents or nitroaryl groups that absorb at longer wavelengths is useful, but use of substituents that absorb at wavelength longer than 450 nm is generally not efficacious for enhancing performance.

A wide range of polymers are useful for producing the subject photosensitive material, provided the polymer is base soluble. As discussed previously, the necessary degree of solubility for the polymer depends on the inhibitor employed. Generally, methacrylate resins, e.g., random copolymers of methyl methacrylate and methacrylic acid are useful. Other polymers, such as novolak resins, carboxylated or sulfonated polystyrenes, and the terpolymers formed from styrene, ethyl or methyl methacrylate, and methacrylic acid are useful. (The latter polymers generally leave a slight residue upon development and, thus, for many operations require a plasma etch to remove this residue.) The polymer employed should be sufficiently soluble in basic solution to yield the desired relative solubility rates. Typically, a polymer having a molecular weight in the range 20,000 to 200,000, preferably 30,000 to 70,000, is employed. Higher molecular weight polymers are less desirable because they have insufficient solubility rates and lower molecular weight polymers are not desirable because they dissolve too readily in the developer, even in the presence of moderate quantities of inhibitors.

The developer used depends on the photosensitive material. Generally, it is desirable to employ a developer whose strength, as measured by the degree of basicity, is just sufficient to dissolve the exposed portions of the photosensitive composite. The necessary strength is easily determined by using a control sample. Exemplary of useful developers is a 10% by weight aqueous solution of $NaHCO_3$ for a 7 mole to 3 mole ratio copolymer of methyl methacrylate and methacrylic acid, a 10% aqueous solution of $Na_2CO_3$ for a 7.4 to 2.6 mole ratio copolymer of methyl methacrylate and methacrylic acid when the inhibitor is o-nitrobenzyl cholate for both of these polymers. An aqueous solution containing 9% $NaHCO_3$ and 1% $Na_2CO_3$ for a 7 to 3 mole ratio copolymer of methyl methacrylate and methacrylic acid is used when the inhibitor is o-nitrobenzyl O,O,O triacetylcholate.

In operation a layer of photosensitive material having a thickness in the range 0.3 to 5 μm is formed on a substrate such as a semiconductor, e.g., a silicon wafer, by conventional techniques, e.g., spinning. (See W. S. Deforrest, *Photoresist Materials and Processes*, McGraw Hill, page 223 (1975) for a description of the spinning process.) After baking the coated wafer, (100 to 180 degrees C., preferably 140 to 160 degrees C., for from 30 minutes to 90 minutes, preferably 45 to 75 minutes) the photosensitive body is exposed through a mask with light in the appropriate wavelength region. The image is then developed by treatment with an appropriate basic material, e.g., the photosensitive body is immersed in an alkaline solution. Typical development times in the range 1 to 10 minutes are employed. It is generally desirable to utilize a treatment time that is not substantially longer than the minimum time necessary to dissolve the exposed region of the photosensitive body. After the pattern is formed in the photosensitive material the substrate, e.g., the wafer, is further processed through conventional steps such as etching and metallization to form the desired devices.

The following examples are illustrative of photosensitive bodies within the subject invention and of process parameters for practice of the invention:

EXAMPLE 1

Polymer Preparation

Approximately 75 ml of methyl methacrylate (0.7 mole) and 25 ml of methacrylic acid (0.3 mole) were dissolved in 350 ml of dry tetrahydrofuran. To this solution was added 81.5 mg of tetrachlorodibromoethane. (This material was added as a chain transfer agent to ensure that the molecular weight of the polymer remained in the desired range.) The solution was then heated to reflux temperature under argon for approximately 1 hour. To this mixture (at reflux temperature) was then added 5 ml of a 70% aqueous solution of t-butyl hydroperoxide. This material acted as a polymerization initiator. Heating at reflux temperature was continued after the addition of the initiator for approximately 4 hours. The heating was then terminated and the reaction mixture was cooled and then was added dropwise to hexane at approximately 2 to 3 drops per second. The polymer precipitated and the liquid was decanted. The remaining polymer was then redissolved in tetrahydrofuran forming a solution which was again added dropwise to hexane. The liquid was decanted and the remaining polymer was air dried.

A terpolymer of methyl methacrylate, methacrylic acid, and styrene was prepared by the procedure described above for the copolymers. Similarly, a terpolymer of ethyl methacrylate, methacrylic acid, and styrene was prepared by the same method as used for the methyl methacrylate-methacrylic acid copolymer. Methyl methacrylate-methacrylic acid copolymers (as described above) were prepared with various molecular weights. (The copolymer in each case had a composition that was approximately 7 moles methyl methacrylate and 3 moles methacrylic acid. The percentage of each monomer incorporated into the polymer was approximately equivalent to the percentage of each present in the reaction mixture.) The adjustment of the molecular weight was done by varying the concentration of the chain transfer agent. The relationship between the chain transfer agent concentration and the final molecular weight is described by Gipstein in *Journal of Polymer Science, Polymer Letters Edition*, 28, page 241 (1980).

For the various polymers made, the percentage of the monomers incorporated in either the copolymer or terpolymer was varied by varying the percentages of the monomers present in the reaction mixture. The values given in Table II are those of the percentage of each monomer present in the reaction mixture. However, the percentage of each monomer incorporated into the polymer does not substantially differ from that used in this reaction mixture.

EXAMPLE 2

Preparation of the Inhibitors (A)

Preparation of o-nitrobenzyl adamantane carboxylate

Approximately 10 g (0.06 mole) of adamantane carboxylic acid was added to 150 ml of ethanol. An equivalent number of moles (2.2 g) of sodium hydroxide also was added to the methanol and the solution was stirred for approximately 15 minutes. This resulted in the formation of sodium adamantane carboxylate. To this reaction mixture was added 7.72 g (0.05 mole) of o-nitrobenzyl chloride. The resulting solution was heated to reflux temperature and stirred at this temperature for 3 hours. The ester thus formed was precipitated by adding 250 ml, in 1 aliquot, of water. The mixture was cooled to ambient temperature and the precipitate was separated by vacuum filtration. The precipitate was recrystallized from 500 ml of a one-to-one by volume solution of ethanol and water to yield approximately 6.4 g of o-nitrobenzyl adamantane carboxylate.

The corresponding o-nitrobenzyl esters of 5$\beta$-cholanic acid (m.p. 53.5–55 degrees C.), fluorenone-4-carboxylic acid (m.p. 210–211 degrees C.), and lithocholic acid (m.p. 160–162 degrees C.) were prepared by the same procedure except that the appropriate acid was employed in place of the adamantane carboxylic acid.

(B)

Preparation of o-nitrobenzyl cholate

Approximately 25 g (0.06 mole) of cholic acid was added to approximately 300 ml of water. About 60 ml of aqueous 1N sodium hydroxide was added to the cholic acid solution. A solution of o-nitrobenzyl bromide in ethanol was prepared by adding 11.05 g (0.03 mole) of the former to 250 ml of the latter. The ethanol solution was then added to the aqueous solution containing the sodium cholate. The combined solution was heated to reflux temperature and stirred at this temperature for about 3 hours. After cooling, the precipitated inhibitor was filtered and recrystallized as described in Section A, except that 750 ml of ethanol-water solution was employed. This procedure yielded approximately 19.5 g of o-nitrobenzyl cholate (m.p. 211 to 213 degrees C.).

Corresponding esters of deoxycholic acid (m.p. 180–181.5 degrees C.) and 12-hydroxydodecanoic acid (m.p. 46–47 degrees C.) were prepared by the same procedure, except that the appropriate acid was substituted for the cholic acid.

(C)

Preparation of o-nitrobenzyl decanoate

A solution formed from approximately 7.2 g (0.1 mole) of decanoic acid, and 15.3 g (0.1 mole) of o-nitrobenzyl alcohol in benzene (100 ml) was prepared. To this solution was added 3 drops of sulfuric acid. The resulting solution was stirred and heated to reflux temperature. The resulting solution was maintained at this temperature for 18 hours and then cooled. Approximately 100 ml of ether was added to the solution and the resulting composition was washed sequentially with 2 aliquots of 100 ml of water, followed by 2 aliquots of a 10% aqueous sodium bicarbonate solution, and finally 1 aliquot of 100 ml of a saturated aqueous sodium chloride solution. The washed benzene-ether solution was then dried over magnesium sulfate. The magnesium sulfate was removed by filtration and the resulting solution was concentrated to an oil by using a rotary evaporator with water aspirator vacuum.

A packed chromatography column was prepared by making a slurry of 200 g of alumina (activity 1, neutral) in hexane. The slurry was put into a column approximately 80 cm in height and 3 cm in diameter. The oil was placed at the top of the column and transported through the column using 500 ml of hexane as an eluant. The eluant was collected and the hexane was evaporated using a rotary evaporator with water aspirator vacuum. This procedure resulted in 12 g of o-nitrobenzyl decanoate.

(D)

Preparation of o-nitrobenzyl N-adamantylphthalamate

A mixture of 25 g (0.17 mole) of phthalic anhydride and 100 ml of toluene was prepared. To this mixture was added a solution of approximately 25.5 g (0.17 mole) of adamantamine in 100 ml of toluene. The resulting mixture was stirred at room temperature for 15 hours. The solid was collected by vacuum filtration and dried in a vacuum oven at room temperature to yield approximately 49 g of N-adamantylphthalamic acid.

The o-nitrobenzyl ester (m.p. 188 to 189 degrees C.) of this acid was prepared by the same procedure as described in Section B of this example where the preparation of o-nitrobenzyl cholate is disclosed.

(E)

Preparation of o-nitrobenzyl O,O,O-tris(trimethylsilyl)cholate

A solution of approximately 2.0 g (3.7 mmoles) of o-nitrobenzyl cholate prepared as described in Section B was dissolved in 20 ml of tetrahydrofuran. Approximately 2.3 ml (11 mmoles) of hexamethyldisilazane and 0.23 ml (1.8 mmoles) of trimethylchlorosilane were added under nitrogen to this o-nitrobenzyl cholate solution. The resulting mixture was stirred at room temperature for approximately 16 hours. The mixture was then gravity filtered. The solid matter was discarded and the filtrate was concentrated on a rotary evaporator at water aspirator pressures to yield o-nitrobenzyl O,O,O-tris(trimethylsilyl)cholate as a tan solid.

(F)

Preparation of o-nitrobenzyl O,O,O-triacetylcholate and o-nitrobenzyl O,O-diacetylcholate Approximately 6.53 g (12 mmoles) of o-nitrobenzyl cholate prepared as described in Section B was dissolved in 50 ml of pyridine. Approximately 15 ml (0.16 mole) of acetic anhydride was added to the solution and the solution was stirred at room temperature for approximately 60 hours. The solution was evaporated to dryness using a rotary evaporator and water aspirator vacuum. The solid residue was dissolved in 200 ml of dichloromethane. The dichloromethane solution was washed sequentially with one 250 ml aliquot of 0.1N HCl, followed by one 250 ml aliquot of deionized water, and one 250 ml aliquot of a 5% aqueous solution of sodium bicarbonate. The dichloromethane solution was then dried over magnesium sulfate for 1 hour and the magnesium sulfate was removed after drying by gravity filtration. The resulting solution was evaporated to dryness on a rotary evaporator using water aspirator vacuum to yield a pale yellow solid. The pale yellow solid was dissolved in boiling methanol and then recrystallized by cooling. The first recrystallization fraction yielded the triesterified material while the second fraction yielded the diesterified compound. If the procedure described in this section was followed, except that the o-nitrobenzyl cholate and acetic anhydride mixture was reacted at 55 to 60 degrees C. for 60 hours, the triesterified material was the sole product.

(G)

The preparation of 4-methoxycarbonyl-2-nitrobenzyl cholate

Approximately 18.1 g of 4-methyl-3-nitrobenzoic acid was added to approximately 50 ml of methanol. Approximately 2 ml of concentrated sulfuric acid was added to this solution. The resulting solution was heated to reflux temperature and stirred at this temperature for 16 hours. The solution was cooled and approximately 300 ml of water was added. The resulting composition was extracted with 200 ml of ether. The ether phase was saved and the aqueous phase was discarded. The ether phase was then sequentially washed with 100 ml of water, followed by 100 ml of 10% aqueous sodium carbonate. The ether phase was dried over magnesium sulfate, filtered, and concentrated using a rotary evaporator and a water aspirator vacuum to yield 17.3 g of 4-methoxycarbonyl-2-nitrotoluene as a viscous oil.

All of the 4-methoxycarbonyl-2-nitrotoluene obtained as described above was dissolved in carbon tetrachloride. Approximately 14.2 g (0.082 mole) of N-bromosuccinimide was added to the carbon tetrachloride solution. The resulting solution was heated to reflux temperature and stirred for approximately 64 hours. The solution was cooled and the succinimide was removed by vacuum filtration. The remaining solution was concentrated on a rotary evaporator using water aspirator vacuum. The synthesis produced 24 g of 4-methoxycarbonyl-2-nitrobenzyl bromide. The cholate ester of this product was then prepared as described for the preparation of the esters in Section B. The O,O,O-triacetyl derivative was also prepared as described in Section F.

EXAMPLE 3

Preparation of Photosensitive Bodies

A spinning solution was prepared by first preparing a 15 weight percent solution of the chosen polymer in cyclopentanone. An amount of the inhibitor equal to 20% of the weight of the polymer was then dissolved in the solution. The solution was filtered through a 0.5 μm filter. Approximately 2 ml of solution was placed on a 3 inch in diameter silicon substrate and the wafer was then spun at approximately 4000 rpm to yield a coating of approximately 1 to 1.5 μm thickness. The coated wafer was then baked at 160 degrees C. for one hour. The various solution inhibitors used in the production of these photosensitive bodies are shown in the following table:

TABLE I

| Parent Acid[a] | Developer[b] | Development Time (Min.) | Thinning (%) | Exposure[c] Time (Min.) | Contrast |
|---|---|---|---|---|---|
| Adamantane Carboxylic Acid | 1 | 15 | 40 | 0.8 | 1.8 |
| 9-Fluorenone-4-carboxylic Acid | 1 | 14 | 75 | 0.8 | ~1.5 |
| Decanoic Acid | 2 | 6 | 60 | 0.8 | 1.6 |
| 12 Hydroxydodecanoic Acid | 1 | 14 | 50 | 0.6 | 1.7 |
| N—Adamantylphthalamic acid | 1 | 16 | 40 | 0.6 | 2.1 |
| Cholic Acid | 3 | 10 | 20 | 0.5 | 2.0 |
| Deoxycholic Acid | 3 | 15 | 20 | 0.6 | 2.0 |
| Lithocholic Acid | 2 | 12 | 15 | 0.7 | 1.6 |
| 5β-Cholanic Acid | 2 | 20 | 25 | 0.8 | 1.5 |
| O,O,O—Tris(trimethylsilyl) cholic Acid | 3 | 10 | 25 | 0.5 | 2.3 |
| O,O,O—Tris(trifluoroacetyl) Cholic Acid | 3 | 10 | 20 | 0.5 | 2.5 |
| O,O—Diacetylcholic Acid | 2 | 10 | 8 | 0.5 | 2.3 |
| O,O,O—Triacetylcholic Acid | 1 | 10 | 0 | 0.5 | 3.2 |
| O,O,O—Tripivaloylcholic Acid | 4 | 10 | 0 | 0.5 | 6.0 |
| Cholic Acid* | 1 | 7 | 20 | 0.6 | 2.0 |
| O,O,O—Triacetyl | 1 | 12 | 0 | 0.6 | 3.0 |

TABLE I-continued

| Parent Acid[a] | Developer[b] | Development Time (Min.) | Thinning (%) | Exposure[c] Time (Min.) | Contrast |
|---|---|---|---|---|---|
| cholic Acid* | | | | | |

[a]The parent alcohol for the esters of the following parent acids was o-nitrobenzyl substituent in all cases except that 4-methoxycarbonyl-2-nitrobenzyl alcohol derivatives are indicated by an asterik.
[b]1, 2, 3, and 4 denote the following developers:
1 = 10% aqueous NaHCO$_3$—Na$_2$CO$_3$ (9:1)
2 = 10% aqueous NaHCO$_3$—Na$_2$CO$_3$ (9.5:0.5)
3 = 10% aqueous NaHCO$_3$
4 = 10% aqueous NaHCO$_3$—Na$_2$CO$_3$ (1:1)
[c]Employing P (MMA—MAA) (70:30) as the polymer.

The photosensitive bodies were exposed using a 1 kW mercury-xenon lamp and an optical system that collected and collimated the light. A quartz step tablet was employed as a contact mask. Irradiation to produce exposure was continued for approximately two minutes. The step tablet allowed various portions of a photosensitive body to be exposed with a progressively larger amount of light. The sensitivity was taken as the least dosage in this stepped progression that allowed development through the thickness of the photosensitive material. The light intensity in the 220±20 nm region was approximately 3 mW/cm$^2$.

The polymer used for the sensitivity data shown in Table I in each case was a copolymer of methyl methacrylate and methacrylic acid from a reaction mixture having seven parts of the former and three parts of the latter (in terms of moles) yielding a molecular weight ($M_w$) 50,760 and a dispersivity ($M_w/M_n$) of 2.23. The sensitivities as measured by the exposure time required obtained for various combinations of inhibitor with this polymer are shown in Table I. Similarly, the contrasts obtained for these photosensitive bodies, as measured by a procedure described in *UV Curing: Science and Technology*, S. P. Pappas, Ed., Technology Marketing Corp., page 333 (1978), are also shown in Table I. To obtain these sensitivities and contrasts, development of the exposed wafers was accomplished by immersing the photosensitive bodies in the respective developers shown in Table I for the time periods also enumerated in Table I. The developed wafers were then rinsed in distilled water for 30 seconds. The developers utilized were chosen to allow development of the exposed region while minimizing the loss of thickness in the unexposed region. The percentage of the total film lost in the unexposed regions is shown under the heading "Thinning" in Table I.

EXAMPLE 4

Effect of Photosensitive Material Composition

The effects of different monomer ratios in the polymer and different ratios between the polymer and inhibitor are shown in the following table:

TABLE II

| Base Resin (Mole Ratio) | $M_w$ | $M_w/M_n$ | Inhibitor[a] (Wt %) | Developer | Development Time (Min.) | Exposure[b] Time (Min.) |
|---|---|---|---|---|---|---|
| Novolak | — | — | 20 | 0.1N NaOH | 1 | 4 |
| P(MMA—MAA) (45:55) | 322,400 | 2.85 | 20 | NaHCO$_3$[c] | 2 | — |
| P(MMA—MAA) (70:30) | 50,760 | 2.23 | 20 | NaHCO$_3$[c] | 10 | 0.5 |
| P(MMA—MAA) (76:24) | 57,590 | 2.24 | 20 | Na$_2$CO$_3$ | 3 | 0.5 |
| P(MMA—MAA) (76:24) | 57,590 | 2.24 | 30 | Na$_2$CO$_3$[c] | 5 | 0.5 |
| P(MMA—MAA) (76:24) | 57,590 | 2.24 | 15 | Na$_2$CO$_3$[c] | 3 | 0.5 |
| P(MMA—MAA) (80:20) | 59,360 | 2.32 | 20 | 0.1N NaOH | 10 | — |
| P(MMA—MAA) (83:17) | 108,400 | 2.63 | 20 | 0.1N NaOH | 10 | — |
| P(MMA—MAA—STY)[f] (58:24:18) | 22,650 | 1.98 | 20 | NaHCO$_3$/Na$_2$CO$_3$ (1:3)[d] | 4 | 0.75 |
| P(EMA—MAA—STY)[f] (54:26:20) | 24,900 | 1.91 | 20 | NaHCO$_3$/Na$_2$CO$_3$ (1:3)[d] | 5 | 1 |
| P(EMA—MAA—STY)[f] (43:38:19) | 34,100 | 2.12 | 20 | NaHCO$_3$/Na$_2$CO$_3$ (7:1)[e] | 3.5 | 1 |

[a]o-nitrobenzyl cholate.
[b]A hyphen indicates MAA content too high or too low to yield suitable sensitivities for typical applications.
[c]10 Wt % aqueous solution.
[d]Aqueous solution with 2.5 Wt % NaHCO$_3$ and 7.5 Wt % Na$_2$CO$_3$.
[e]Aqueous solution with 8.75 Wt % NaHCO$_3$ and 1.25 Wt % Na$_2$CO$_3$.
[f]STY is an abbreviation for styrene and EMA is an abbreviation for ethyl methacrylate.

The polymers were prepared as described in Example 1. The inhibitors were prepared as described in Example 2, and the photosensitive bodies were prepared as described in Example 3. For each case, the developer employed, the exposure times required, and the molecular weight and dispersivity of the polymer are listed in Table II.

EXAMPLE 5

Effect of Molecular Weight

The effect of varying the molecular weight of the polymer is shown in Table III. The polymer was prepared from a 7 to 3 mole ratio solution mixture of methyl methacrylate and methacrylic acid reacted as described in Example 1. The inhibitor employed was o-nitrobenzyl cholate prepared as described in Example 2. The photosensitive bodies were prepared as described in Example 3. The developer employed, the percentage thinning in the unexposed region, and the sensitivity obtained are listed in Table III.

TABLE III

| Molecular Weight ($M_w/M_n$) | Developer | Development Time (Min.) | Thinning (%) | Exposure Time (Min.) |
|---|---|---|---|---|
| 216,900 (1.69) | NaHCO$_3$* | 20 | 10 | 1.5 |
| 50,760 (2.23) | NaHCO$_3$* | 10 | 20 | 0.5 |

TABLE III-continued

| Molecular Weight ($M_w/M_n$) | Developer | Development Time (Min.) | Thinning (%) | Exposure Time (Min.) |
|---|---|---|---|---|
| 21,590 (3.11) | NaHCO$_3$* | 2.5 | 50 | 0.5 |

*10% aqueous solution

EXAMPLE 6

The preparation of o,o'-dinitrobenzyl cholate

O,o'-dinitrotoluene (7.84 grams, 0.08 moles) was dissolved in carbon tetrachloride. Approximately 14.2 grams (0.082 moles) of N-bromosuccinimide was added to the carbon tetrachloride solution. The resulting solution was heated to reflux temperature and stirred for approximately 48 hours. The solution was cooled and the succinimide was removed by vacuum filtration The remaining solution was concentrated on a rotary evaporator using water aspirator vacuum. The synthesis produced 10 grams of o,o'-dinitrobenzyl bromide. The cholate ester of this product was then prepared by initially adding approximately 25 grams (0.06 moles) of cholic acid to approximately 300 ml of water. About 60 ml of aqueous 1N sodium hydroxide was added to the cholic acid solution. A solution of o,o'-dinitrobenzyl bromide and ethanol was prepared by adding 5.04 grams (0.03 moles) of the former to 250 ml of the latter. The ethanol solution was then added to the aqueous solution containing the sodium cholate. The combined solution was heated to reflux temperature and stirred at this temperature for about 3 hours. After cooling, the precipitated ester was filtered and recrystallized from 750 ml of a 1-to-1 by volume solution of ethanol and water to yield approximately 9 grams of o,o'-dinitrobenzyl cholate.

Preparation of photosensitive bodies

A spinning solution was prepared by first preparing a 15 weight percent solution of P(MMA-MAA) (7.5:2.5) (molecular weight equal to 67 × 10$^3$) in cyclopentanone. An amount of o,o'-dinitrobenzyl cholate equal to 20 percent of the weight of the polymer was then dissolved in the solution. The solution was filtered through a 0.5 μm filter. Approximately 2 ml of solution was placed on a 3 inch in diameter silicon substrate, and the wafer was then spun at approximately 4000 rpm to yield a coating of approximately 1 μm thickness. The coated wafer was then baked at 160 degrees C. for one hour.

The photosensitive bodies were exposed using a 500 W mercury-xenon lamp in an optical system that collected and collimated the light. A quartz step tablet was employed as a contact mask. Irradiation to produce exposure was continued for approximately two minutes. The step tablet allowed various portions of the photosensitive body to be exposed with a progressively larger amount of light. The sensitivity was taken as the least dosage in this stepped progression that allowed development through the thickness of the photosensitive material. The light intensity in the 260±20 nm region was approximately 10 mW/cm$^2$.

The sensitivity and contrast obtained for the system were, respectively, 90 mJ/cm$^2$ and 5. These values were obtained by development of the exposed wafers in 10 percent aqueous sodium carbonate for 3 minutes followed by a rinse in distilled water for 30 seconds. The developer was chosen to allow development of exposed regions while minimizing the loss of thickness in the unexposed regions.

What is claimed is:

1. A photosensitive body comprising a substrate and a photosensitive material characterized in that
   said photosensitive material comprises a mixture of a polymer which is soluble in an alkaline composition and an o,o'-dinitroarylmethyl ester of a carboxylic acid represented by the formula

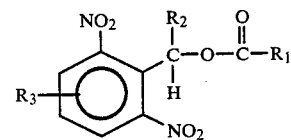

where R$_1$ is a substituent chosen so that a salt of the carboxylic acid, R$_1$COOH, is sufficiently soluble in water to produce at least a 0.01M solution and R$_1$, R$_2$, and R$_3$ are chosen so that when said photosensitive body is irradiated with electromagnetic radiation, the ratio expressed as 1:n of the solubility rate of the unexposed to the exposed portions is such that n is at least 4.

2. The body of claim 1 wherein said substrate is a silicon wafer.

3. The body of claim 1 wherein R$_1$ corresponds to the R$_1$ in the carboxylic acid, R$_1$COOH and wherein said carboxylic acid is chosen from the group consisting of N-adamantylphthalamic acid, cholic acid, deoxycholic acid, lithocholic acid, 5β-cholanic acid, O,O,O-tris(trimethylsilyl)cholic acid, O,O,O-tris(trifluoroacetyl)cholic acid, O,O,O-triacetylcholic acid, O,O,O-tripivaloylcholic acid, and O,O-diacetylcholic acid.

4. The body of claim 1 wherein said o,o'-dinitroarylmethyl ester is an o,o'-dinitrobenzyl ester.

5. The body of claim 1 wherein the value n in said ratio is at least 10.

6. The body of either claim 4, 2 or 1 wherein said polymer comprises a copolymer of methyl methacrylate and methacrylic acid.

7. The body of claim 1 wherein the amount of said o,o'-dinitroarylmethyl ester relative to said polymer in said photosensitive material is in the range 5 to 40 weight percent.

* * * * *

UNITED STATES PATENT AND TRADEMARK OFFICE
CERTIFICATE OF CORRECTION

PATENT NO. : 4,666,820

DATED : May 19, 1987

INVENTOR(S) : Edwin A. Chandross, Elsa Reichmanis, and Cletus W. Wilkins, Jr.

It is certified that error appears in the above-identified patent and that said Letters Patent is hereby corrected as shown below:

Column 3, line 55, "sufficient" should read --sufficiently--.

Signed and Sealed this

Twenty-sixth Day of January, 1988

Attest:

DONALD J. QUIGG

Attesting Officer     Commissioner of Patents and Trademarks